United States Patent [19]
Bischof et al.

[11] Patent Number: 6,121,508
[45] Date of Patent: Sep. 19, 2000

[54] POLAR, LIPOPHILIC PRESSURE-SENSITIVE ADHESIVE COMPOSITIONS AND MEDICAL DEVICES USING SAME

[75] Inventors: Katharina J. Bischof, Leichlingen; Wilhelm Kuester, Kaarst, both of Germany; Steven S. Kantner, St. Paul, Minn.

[73] Assignee: 3M Innovative Properties Company, St. Paul, Minn.

[21] Appl. No.: 09/091,783

[22] PCT Filed: Dec. 29, 1995

[86] PCT No.: PCT/US95/16996

§ 371 Date: Jun. 22, 1998

§ 102(e) Date: Jun. 22, 1998

[87] PCT Pub. No.: WO97/24149

PCT Pub. Date: Jul. 10, 1997

[51] Int. Cl.[7] ....................................... A61F 13/00
[52] U.S. Cl. ................. 602/52; 602/51; 602/56; 602/58; 428/355 R; 428/355 AC
[58] Field of Search ............... 602/56, 51, 52, 602/58; 428/355 R, 355 AC

[56] References Cited

U.S. PATENT DOCUMENTS

| | | | |
|---|---|---|---|
| 3,845,757 | 11/1974 | Weyer | 128/2.1 E |
| 3,991,002 | 11/1976 | Sadlo | 260/32.8 A |
| 4,080,348 | 3/1978 | Korpman | 260/27 BB |
| 4,215,696 | 8/1980 | Bremer et al. | 128/641 |
| 4,274,420 | 6/1981 | Hymes | 128/641 |
| 4,492,725 | 1/1985 | Ishihara et al. | 428/69 |
| 4,497,914 | 2/1985 | Allen, Jr. et al. | 523/105 |
| 4,524,087 | 6/1985 | Engel | 427/2 |
| 4,539,996 | 9/1985 | Engel | 128/640 |
| 4,581,821 | 4/1986 | Cahalan et al. | 29/877 |
| 4,588,762 | 5/1986 | Mruk et al. | 524/45 |
| 4,593,053 | 6/1986 | Jevne et al. | 523/111 |
| 4,674,512 | 6/1987 | Rolf | 128/640 |
| 4,684,558 | 8/1987 | Keusch et al. | 428/40 |
| 4,699,146 | 10/1987 | Sieverding | 128/640 |
| 4,750,482 | 6/1988 | Sieverding | 128/156 |
| 4,777,954 | 10/1988 | Keusch et al. | 128/640 |
| 4,830,776 | 5/1989 | Thompson | 128/640 |
| 4,848,353 | 7/1989 | Engel | 128/640 |
| 5,002,792 | 3/1991 | Vegoe | 427/2 |
| 5,024,227 | 6/1991 | Schmid | 128/640 |
| 5,049,608 | 9/1991 | Medina | 524/375 |
| 5,116,676 | 5/1992 | Winslow | 428/343 |
| 5,183,841 | 2/1993 | Bernard | 524/272 |
| 5,409,966 | 4/1995 | Duan et al. | 522/152 |
| 5,785,985 | 7/1998 | Czech et al. | 424/448 |
| 5,846,558 | 12/1998 | Nielson et al. | |

FOREIGN PATENT DOCUMENTS

| | | |
|---|---|---|
| 0 184 470 B1 | 6/1986 | European Pat. Off. ........ A61L 15/16 |
| 0 271 292 A2 | 6/1988 | European Pat. Off. ........ A61L 15/06 |
| 0 351 193 A2 | 1/1990 | European Pat. Off. ........ C08L 33/08 |
| 0 399 432 A2 | 11/1990 | European Pat. Off. ........ A61L 15/16 |
| 3609 137 A1 | 9/1987 | Germany . |
| 3917 018 C2 | 8/1991 | Germany ................ C08F 2/44 |
| 2 119 254 | 11/1983 | United Kingdom .......... A61B 5/04 |
| WO 91/05509 | 5/1991 | WIPO ................ A61B 5/0408 |

OTHER PUBLICATIONS

Derwent Abstract of Japanese Publication JP 2235808 A (1990).

*Primary Examiner*—John G. Weiss
*Assistant Examiner*—Kelmar Hart
*Attorney, Agent, or Firm*—Eloise J. Maki

[57] ABSTRACT

A hydrophilic, pressure-sensitive adhesive composition prepared by irradiating solid poly(N-vinyl lactam) with ionizing radiation to crosslink the poly(N-vinyl lactam) and thereafter mixing the radiation-crosslinked poly(N-vinyl lactam) with essentially unirradiated plasticizer in an amount sufficient to form a cohesive, pressure-sensitive adhesive composition. The composition is useful as a biomedical adhesive for transmitting or receiving electrical signals as a component (14) of a biomedical electrode (10).

28 Claims, 2 Drawing Sheets

POLAR, LIPOPHILIC PRESSURE-SENSITIVE ADHESIVE COMPOSITIONS AND MEDICAL DEVICES USING SAME

FIELD OF THE INVENTION

This invention relates to polar, lipophilic pressure-sensitive adhesive compositions for contacting a variety of types of mammalian skin. In another aspect, the invention relates to a biomedical electrode having a pressure-sensitive adhesive as the ionically-conductive, skin interfacing material. In another aspect, the invention relates to skin-contacting medical articles that include either a drug in the adhesive composition to form a transdermal delivery device or an anti-microbial agent as a wound dressing.

BACKGROUND OF THE INVENTION

Pressure-sensitive adhesives find broad utility in skin-contacting medical applications providing the means for reversibly securing tapes, dressings, and devices to the patient as detailed in "Porous and Other Medical Pressure Sensitive Adhesives", K. Krug and N. M. Marecki, Adhesives Age, p. 19, November 1983 and "Hospital and First Aid Products", D. Satas and A. M. Satas, Chapter 25 in Handbook of Pressure Sensitive Adhesive Technology, Second Edition, D. Satas, Editor, Van Nostrand, Rheinhold, 1989.

An adhesive composition can also serve to adhere a biomedical electrode to skin and to establish an electrical connection between skin and an electrical medical apparatus desirably has multiple characteristics that are difficult to achieve in one composition. The composition should have the characteristics of a good medical adhesive and those of a good electrical conductor. Electrical conductivity is imparted by ionic species in polar adhesive compositions.

Ionically-conductive, pressure-sensitive adhesives suitable for use in many biomedical electrodes are shown in many patents. U.S. Pat. No. 4,524,087; U.S. Pat. No. 4,539,996; U.S. Pat. No. 4,554,924; U.S. Pat. No. 4,581,821; U.S. Pat. No. 4,674,512; U.S. Pat. No. 4,777,954; U.S. Pat. No. 4,684,558, and U.S. Pat. No. 4,848,353 are exemplary.

Ionically-conductive adhesives made according to the above listed patents are used in patient grounding plates, transcutaneous electrical nerve stimulation (TENS) electrodes, and diagnostic electrocardiogram (EKG/ECG) electrodes. While these adhesives provide adequate adhesive and electrical properties for some applications, optimizing the electrical properties without adversely affecting adhesion properties has been difficult. It is known that increasing the water content of the adhesive compositions described in the above mentioned U.S. patents to about 25% improves the electrical performance of electrodes coated with the adhesives. The reason for this empirical observation is not known. One possible explanation is that the increased water facilitates hydration of skin, thereby reducing skin impedance. Unfortunately, increasing water content to optimum levels for electrical performance is found to decrease the tack of the adhesive, resulting in lower skin adhesion.

Another ionically-conductive adhesive is disclosed in GB-A-2,115,431 and U.S. Pat. Nos. 4,699,146 and 4,750,482. The adhesives described therein are formed by dissolving or dispersing polymers in a plasticizing liquid and subjecting the mixture to radiation energies at least equivalent to 100,000 electron volt (X-ray, gamma and beta ray, and electron beam irradiation). Present with the polymers are irradiation-compatible, nonvolatile elasticizers that among others include mono- or diethers of a polyalkylene glycol, mono- or diesters of a polyalkylene glycol, and an imidazoline derivative amphoteric surfactant. But cautions are also provided not to permit plasticizers containing surfactants or detergents from contacting skin, in order to assure that the adhesive is hypoallergenic and not skin irritating. These patents also fail to recognize the beneficial effect of having such surfactants or detergents present in a polar adhesive to allow for absorption of skin oil away from the adhesive/skin interface providing better bond formation. Indeed these patents caution that such materials are better employed so as not to be in contact with skin, in order to assure that skin irritation is not caused.

Mammalian skin naturally exudes a variety of oils and other lipophilic compounds that protect the skin. Human skin surface lipids are produced both by sebaceous gland activity and by the epidermis as noted in "Sebaceous Glands", John S. Strauss, Donald T. Downing, and F. John Ebling, p. 569, Chapter 26 of Biochemistry and Physiology of the Skin, Lowell A. Goldsmith, editor, Oxford University Press, New York, 1983. Areas rich in sebaceous glands have a higher total lipid concentration, ranging in one study from a high of 160 micrograms/sq cm on the forehead to 19 micrograms/sq cm on the leg. Moderate levels are seen on the chest (59 micrograms), side (29 micrograms) and arm (30 micrograms) which along with the leg are areas of application of the biomedical electrodes which are one of the uses for the adhesive of the present invention. The composition of these lipids varies somewhat dependent on the relative contributions of these two sources with areas rich in sebaceous glands having higher concentrations of wax esters and squalene. Major components in the skin surface lipids include triglycerides (average 30%), free fatty acids obtained from bacterial hydrolysis of the triglycerides (average 30%), wax esters (20%), and squalene (10%). The fatty acids that make up the triglycerides are predominately linear saturated C16 (palmitic acid, 24%), mono-unsaturated C18 (oleic acid, 36%), mono-unsaturated C16 (9%) and linear saturated C18 (stearic acid, 8%) according to C. Carruthers, in Biochemistry of Skin in Health and Disease, Chapter 4, "Lipid Composition", p. 73, Charles C. Thomas Publisher, Springfield, Ill., 1962. This layer of skin surface lipid serves as a weak boundary layer, limiting the ability of a pressure sensitive adhesive to rapidly for a bond with the skin. A pressure sensitive adhesive, such as an acrylate or rubber-resin based material, may absorb the skin oil away from the interface allowing for bond formation. Polar adhesives, such as those ionically conductive adhesives cited above, tend to be incompatible with the oil, leading to surface detackification and poorer bond formation.

SUMMARY OF THE INVENTION

There is a need to provide a polar pressure sensitive adhesive that can reliably adhere to a wide variety of skin types (oily, hairy, dirty, diaphoretic, moist, dry, . . . ) both immediately and for up to a week and yet be removed after use without causing undue trauma to the skin.

The prior art has not recognized or successfully addressed this problem of continued, reliable adhesion in the presence of a variety of skin types, especially oily skin. This problem remains a significant challenge to the adhesive manufacturer and may be further complicated by the fact that the adhesive may be required to do more than just bond to the skin.

For example, pressure-sensitive adhesives used in transdermal drug delivery devices may also serve as a reservoir for the drug. Pressure-sensitive adhesives used in wound dressings may require high moisture vapor transmission rates to prevent skin maceration and aid healing. Pressure-sensitive adhesives used in biomedial electrodes may need to be ionically-conductive.

The present invention solves the problem unrecognized or unaddressed by the prior art. The present invention provides a polar, lipophilic, pressure-sensitive adhesive that maintains adhesiveness in the presence of oily mammalian skin.

The pressure-sensitive adhesive composition preferably comprises a skin compatible, lipophilic, polar pressure-sensitive adhesive, comprising a hydrophilic polymer matrix and a plasticizer in an amount sufficient to render the matrix cohesive and pressure-sensitive adhesive. The plasticizer comprises a water-soluble polar organic compound and at least 9 weight percent of the adhesive of a compatible surfactant having a HLB-value of 10 to 17 or mixture of compatible surfactants combining to have a HLB-value of 10 to 17.

Surprisingly it has been found that the use of a compatible surfactant as a portion of the plasticizer creates a phase in the adhesive that imparts structural strength to the adhesive composition, reduces moisture sensitivity in the adhesive composition, and also allows the adhesive composition to absorb oily substances away from the adhesive/substrate interface into the bulk of the adhesive resulting in improved bond formation and retention.

For the purposes of this invention, a "compatible" surfactant is a surfactant that acts as a cosolvent for the hydrophilic polymer matrix such that the mixture of water soluble, polar organic compound, surfactant, and water when used solvate and swell the hydrophilic polymer matrix forming a macroscopically homogeneous composition with no gross phase separation of liquid or solid. When the mixture of surfactant, polar organic compound, and water when used is compatible with the polymeric matrix it functions as a plasticizer, observed experimentally by a depression in the glass transition temperature. Alternatively, in incompatible systems the surfactant may bloom to the surface, causing detackification of the adhesive.

While not being limited to a particular theory, the ability of the adhesive to absorb oil away from the interface (hence eliminating a weak boundary layer) and the rate at which that oil is absorbed into the bulk (which determines the speed of bond formation) is determined by the nature and quantity of the surfactant used. As noted in Chapter 3 of *Surfactant Science and Technology,* Drew Meyers, VCH Publishers, New York, 1988, as the amount of surfactant is increased beyond relatively low concentrations (where only monomers and micelles exist), liquid crystalline structures or mesophases are encountered. These mesophases may take the form of bilayered lamellar phases. We believe that this lamellar structure allows for rapid absorption of skin oil into the polar adhesive by providing non-polar conduits into the bulk. Mesophases are normally lyotropic, meaning that the characteristics of the system are highly dependent on the nature and amount of solvent present. Addition of further components such as an electrolyte, the polar organic compound, and the hydrophilic polymeric network will alter the thermodynamic balance of the system and will, as a result, alter the nature of the aggregated species present. Because of these interactions it is difficult to predict utility of a given surfactant for preparation of the adhesive compositions of the present invention.

The pressure-sensitive adhesive compositions of the present invention may be prepared by generating a hydrophilic polymeric matrix in the presence of the plasticizing solution using polymerization or crosslinking techniques or by first generating the hydrophilic polymer matrix and then mixing it with the plasticizing solution to yield the adhesive. Preferably the hydrophilic polymer matrix is formed from a free radically polymerizable adhesive precursor having at least one water-soluble monomer and a free radical initiator of the photo or thermal class. Alternatively the matrix can be formed by a crosslinking of polymers having random pendent Functionality of photoactive pendent groups (such as photoactive benzophenones or photoinitiable (meth) acrylates) according to copending, coassigned PCT Patent Application 95/16993 (Attorney's Docket No. 51290PCT8A).

The composition does not need to be covalently crosslinked, but a crosslinker may be used. A multifunctional crosslinker may be added to the adhesive precursor up to about 1.5 weight %.

Embodiments of the invention are described below, in part in conjunction with the following drawings.

EMBODIMENTS OF THE PRESENT INVENTION

Figure 1:
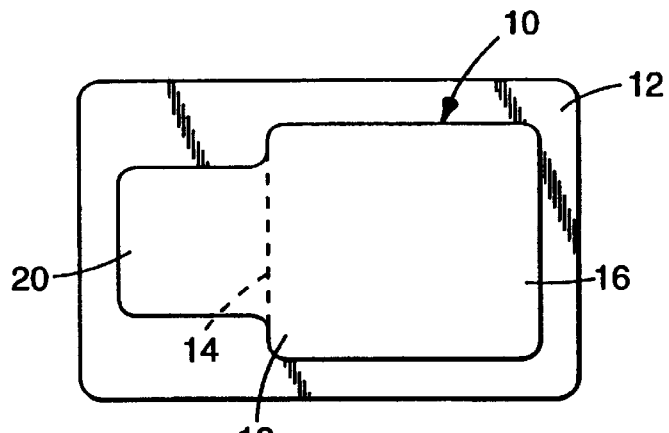
FIG. 1 is a top plan view of a biomedical electrode containing an adhesive composition of the present invention, used for diagnosis or monitoring of heart conditions of a mammalian patient.

Preferably, the hydrophilic polymer matrix may be selected from the group consisting of poly(ethylene oxide), natural and synthetic polysaccharides and their derivatives, and homo- and copolymers of ethylenically unsaturated hydrophilic monomers including $\alpha,\beta$-ethylenic unsaturated carboxylic acids having 3 to 8 carbon atoms and salts thereof such as (meth)acrylic acid and salts thereof, acrylamide, N-vinyl pyrrolidone, hydroxyethyl (meth)acrylate, acrylamidopropane sulfonic acid and salts thereof, methyl and ethyl vinyl ether, and polymers having ammonium functionality derived from reaction of amine containing monomers with alkylating agents or protic acids, for example N,N'-dimethylaminoethyl (meth)acrylate and vinyl pyridine. In a preferred embodiment of the present invention the polymer matrix contains a homo- or copolymer of acrylic acid, wherein the acidic groups may be preferably neutralized from 0.5 to 95% in accordance with the teachings of U.S. Pat. No. 4,848,353. Alkali hydroxides may be used as a neutralizing agent for the acidic groups, sodium and potassium hydroxide being preferred.

The hydrophilic polymeric matrix can comprise from about 10 to about 40 weight percent of the adhesive composition of the present invention, and preferably may comprise from about 20 to about 35 weight percent. Compositions containing this level of hydrophilic polymeric matrix have a desirable balance of tack, softness, adhesiveness, and cohesive strength. The composition has substantially a homogeneous appearance, i. e. the aqueous, liquid phase is retained in the polymeric matrix, and essentially no phase separation can be observed with the eye.

The plasticizing solution is compatible with the polymer matrix and comprises from about 0 to 80 weight percent water-soluble, polar organic compound, about 0 to 60 weight percent water and at least 10 weight percent of a surfactant or mixture of surfactants. All of these weight percents are based on the total weight of the adhesive composition.

As a compatible surfactant an anionic, cationic, nonionic or amphoteric surfactant may be used. The use of such surfactants improves the adhesion of the pressure-sensitive adhesive electrodes to oily skin by giving the adhesive lipophilic properties. By incorporating the surfactants into the adhesive the compatibility between the adhesive and the oily skin is improved.

Suitable anionic compatible surfactants include alkyl benzene sulfonates, alkyl sulfonates, olefin sulfonates, alkyl ethersulfonates, glycerol ethersulfonates, α-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates and alkyl (ether)phosphates.

Suitable nonionic compatible surfactants include fatty alcohol polyglycolethers, alkyl phenylpolyglycolethers, fatty acid polyglycolesters, fatty acid amide polyglycolethers, fatty amine polyglycolethers, alkoxylated triglycerides, alk(en)yl oligoglycosides, fatty acid glucamides, polyol fatty acid esters, sugar esters, sorbitol esters and sorbitol ester ethoxylates and polysorbates.

Suitable cationic compatible surfactants include quaternary ammonium compounds and quaternized difatty acid trialkanol amine esters.

Suitable amphoteric compatible surfactants include alkyl betaines, alkyl amidobetaines, amino propionates, amino glycinates, imidazolinium betaines and sulfobetaines.

Preferred compatible surfactants may be selected from nonionic surfactants having an HLB-value of 10 to 17. Fatty alcohol polyglycolethers, sorbitol fatty acid esters, and sorbitol fatty ester ethoxylates in this HLB range are particularly preferred. As is known to those skilled in the art, the HLB-value is an acronym for the hydrophilic-lipophilic balance and indicates the extent to which a given surfactant will behave as an oil-soluble vs. a water-soluble type of emulsifier as described in Chapter 20 of *Surface Active Agents and Detergents,* Volume II, Anthony M. Schwartz, James W. Perry, and Julian Berch, Robert E. Krieger Publishing Co., Huntington, N.Y., 1977. HLB-values in this range help assure that the surfactant is soluble in the adhesive formulation and also have high enough hydrocarbon content to impart desired oil absorbancy at lower usage.

The water-soluble, polar organic compound of the plasticizing solution has the function of a humectant and is used as means for retaining sufficient water within the aqueous phase of the adhesive to keep the electrolyte salts dissolved and ionized if an ionically conductive adhesive is desired or to keep drug in solution if a transdermal delivery device is desired or to keep anti-microbial agents in solution if a wound dressing is desired. The water-soluble, polar compound may be selected from a compound consisting of mono- and polyhydric alcohols. Low molecular weight polyoxyethylene glycols are suitable (average molecular weight up to 600, e. g. Carbowax™ 200 and 600 available from Union Carbide). Among these compounds glycerol, poly(ethylene glycol), monomethoxypoly(ethylene glycol) and propanediol are preferred because they give good adhesive performance and good water retention.

The adhesive composition of the present invention can contain the water-soluble, polar organic compound in an amount up to 80 weight percent, preferably 10 to 50 weight percent and water in an amount up to 60 weight percent and preferably 10 to 30 weight percent. When present in these preferred amounts, water and the polar organic compound provide adhesive compositions with a good balance of pressure sensitive adhesive performance while maintaining good ionic conductivity.

The adhesive composition of the present invention can also contain up to 12 weight percent of a water-soluble salt such as alkali and alkaline earth halides, acetates, phosphates, and sulfates that impart conductivity to adhesive compositions based on nonionic polymer matrices or enhance conductivity of adhesive compositions that contain ionic polymer matrices. Those skilled in the art of making and using biomedical electrodes will appreciate that when the polymer matrix contains hydrogen donating monomers (e.g., acrylic acid) and those monomers are above 20 percent neutralized, the salts of such monomers dissociate in the presence of water of the plasticizing solution into ionic species and result in a final adhesive composition that is sufficiently ionically conductive for use on grounding plate electrodes. However, where the intended use is on monitoring biomedical electrodes having the ability to recover from potential overloads applied during defibrillation, it is preferred that a chloride containing salt, such as potassium or sodium chloride, in an amount between about 0.5 and 3 weight percent of the adhesive composition, be present in the adhesive composition and that the adhesive composition be used with a silver/silver chloride conductor.

It has been found that the adhesiveness and peel adhesion of the pressure-sensitive adhesive compositions of the present invention can be improved by incorporating components having the ability to adsorb body fluids such as sweat from patient skin and to retain water. That means, in practical application such component adsorbs water (e.g. sweat) from patient skin, thus a decrease of the adhesion of the composition to the skin does not occur. Another advantage is, water is retained in the composition. Usually, when a package of adhesives, for example electrodes, is opened the adhesive composition dries out when not all of them are used immediately. When using the adhesive composition of present invention water is retained and drying out of the electrodes is minimized. Different kinds of components having such properties are useful in the adhesive composition of present invention and may be selected from the group of cellulose and its derivatives, starch and its derivatives and pectins of different origin. These components may be used in an amount up to 10 by weight, most preferably 1 to 8% by weight.

Preferably, the water adsorbing components are selected from the group consisting of natural polysaccharides such as karaya gum, agar-agar (polysaccharide); crosslinked dextran (for example Sephadex, a product of Pharmacia Fine Chemicals, AB, Upsalla, Sweden); cellulose and modified cellulose polymers such as sodium carboxy methyl cellulose, hydroxyethyl cellulose, crosslinked sodium carboxy methylcellulose; starch and synthetically modified starch polymers such as sodium starch glycolates; guar gum; pectin (glycoside); gelatin; carrageenan; etc. Alternatively crosslinked poly(N-vinyl lactams) can be used in accordance with U.S. Pat. No. 5,362,420 (Itoh et al.). These various materials can also be used to thicken the precursor prior to coating the precursor on the substrate.

In a preferred embodiment the composition of present invention has covalent crosslinking. In that case the adhesive precursor includes a multifunctional monomer. Suitable crosslinkers include triethylene-glycol-bismethacrylate (TEGBM), ethylene-glycol-bis-methacrylate, methylene bis-acrylamide, tetraethylene-glycol-diacrylate (TEGDA), and 3,3'-ethylidene-bis(N-vinyl-2-pyrrolidone). Additional crosslinkers are listed in U.S. Pat. No. 4,536,554. The amount of the crosslinker may be varied depending on the choice of monomers and crosslinkers and the polymerization conditions. When the monomers are acrylic acid and/or N-vinyl-pyrrolidone, the crosslinker is preferably triethylene-glycol-bismethacrylate (TEGBM) or tetraethylene-glycol-diacrylate (TEGDA). Crosslinker levels from 0.2 to 0.9% by weight of total monomers may be conveniently used.

The present invention also provides a process for the preparation of the pressure-sensitive adhesive composition. The pressure-sensitive adhesive compositions of the present invention may be obtained by subjecting a curable composition comprising 10 to 40 weight-% of a hydrophilic, ethylenically unsaturated monomer curable to the hydrophilic polymer matrix dissolved to make a solution with up to 60 weight percent water, up to 80 weight percent water-soluble, polar organic compound, and at least 10 weight percent of a surfactant or a mixture of surfactants and a polymerization initiator for the hydrophilic monomer to free radical polymerization conditions. For dissolving the monomers in the plasticizing solution, the components may be mixed together. Optionally the curable composition also may contain the above defined components such as water-soluble salt, one or more water adsorbing components and a crosslinker.

The polymerization may be started with an initiator of either the photo or thermal class. Photoinitiators are preferred. Examples of useful photoinitiators are disclosed in the article "Photoinitiators—An Overview" by Berner et al., in the Journal of Radiation Curing (April 1979, pp. 2 through 9). The preferred photoinitiator is 2,2-dimethoxy-2-phenylacetophenone. Examples of useful thermal initiators are $K_2S_2O_8$, benzoyl peroxide, azo-bis-isobutyronitrile, di-t-butyl peroxide and bromyl peroxide. The actual selection of initiator is dependent on the monomers and other components of the adhesive precursor.

In the process for the preparation of the adhesive composition of the present invention the materials present in the precursor are present in the same or modified form in the final composition. The plasticizing solution can serve as a solvent for the monomers in the polymerization step and can be present as the plasticizing liquid in the final composition.

As explained above, the obtained copolymer matrix may be, but need not be, covalently crosslinked. Preferably, a difunctional crosslinking monomer is included and polymerization is carried out to substantial completion leaving less than 1% monomer in the final composition. The process may be carried out in situ with the adhesive precursor coated on an electrode conductor or backing substrate. Alternatively the adhesive precursor can be coated on a transfer sheet to make a web of adhesive that subsequently may be incorporated into a composite such as a biomedical electrode. In latter case, the adhesive precursor is preferably coated and cured on a thin scrim, e. g. 0.1 mm Cerex™ material (Monsanto), to facilitate mechanical handling in the manufacturing process.

The process of the present invention can also employ crosslinking via random pendent functionality of photoreactive pendent groups or photoinitiable pendent groups, such as that disclosed in copending, coassigned PCT Patent Application Serial No. 95/16993 (Attorney's Docket 51290PCT8A). Briefly, that method comprises preparing polar polymers via thermal polymerization with copolymerizable pendent photoreactive moieties that undergo activation to provide crosslinked hydrophilic pressure sensitive adhesives when plasticized with humectants. When this pendent photoactive moiety is obtained from a "system soluble", (meth)acrylated photoinitiator, very rapid, reproducible, and complete crosslinking can be obtained with high intensity UV lights allowing for efficient manufacture of adhesive coated articles and tapes, especially when thick coatings of adhesive are desired. These materials are particularly suited for use as skin contacting pressure sensitive adhesives for medical use where high moisture vapor transmission rates or ionic conductivity may be important. "System soluble" means that the photoinitiator is soluble in a mixture of water, plasticizer, and monomer at a temperature used in copolymerization. In order for the resulting swollen network to possess a degree of pressure sensitive tack, the functionalized polar polymer should be present in an amount of about 10 to 40 weight percent with plasticizer being present in amount of about 90 to 60 weight percent. The polar polymer can contain from about 95 weight percent to 99.5 weight percent, preferably 97 weight percent to 99 weight percent, hydrophilic monomer and from 0.5 weight percent to 5 weight percent, preferably 1 to 3 weight percent, of system soluble (meth)acrylated photoinitiator.

Usefulness of the Invention

Adhesive compositions of the present invention can be used in a variety of applications where pressure sensitive adhesives are industrially or commercially applied in the manufacture of tapes, adhesive substrates, and the like. Preferably, adhesive compositions of the present invention can be used in the field of health care where adhesive requirements are particularly stringent and difficult when adhesion to oily mammalian skin is involved.

Because mammalian skin is a particularly difficult surface to identify and control acceptable adhesive properties, the adhesive composition of the present invention is particularly suitable for use in mammalian skin covering applications such as biocompatible medical adhesives such as for receipt or delivery of electrical signals at or through mammalian skin, delivery of pharmaceuticals or active agents to or through mammalian skin, or treatment of mammalian skin or mammalian skin openings against the possibilities of infection.

Biomedical Electrodes

Biomedical electrodes employing adhesive compositions of the present invention having electrolyte contained therein are useful for diagnostic (including monitoring) and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

Figure 2:
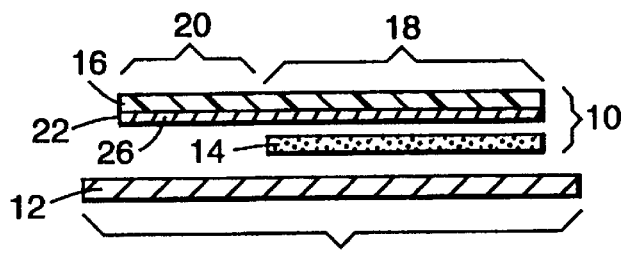
FIG. 2 is a cross-sectional view of the biomedical electrode of FIG. 1.

FIGS. 1 and 2 show either a disposable diagnostic electrocardiogram (ECG or EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred for conductor member 16 are polyester films commercially available as Scotchpak™ brand film from Minnesota Mining and Manufacturing Company of St. Paul, Minn. or "Melinex" 505-300, 329, or 339 brand film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" material from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Alternatively, conductor member can be a multi-layered construction of a nonconductive, flexible polymeric film having a sulfur-reactive surface, a metallic layer deposited on and interacting with the surface and an optional metallic halide layer, according to the disclosure of PCT Publication WO 94/026950, the disclosure of which is incorporated by reference herein. The conductive interface portion 18 of member 16 comprises a metallic layer deposited on a sulfur-reactive surface on at least the side of polymeric film substrate facing field 14 of the conductive medium and the optional metallic halide layer coated on the metallic layer and contacting field 14. Because depolarizing is not needed for the mechanical and electrical contact with electrical equipment, the optional metallic halide layer does not need to extend to tab portion 20.

Alternatively, conductor member 16 can be a multi-layered construction of a nonconductive, flexible polymeric film, an electrically conductive layer, and a thin, conformable depolarizing layer of inorganic oxide, preferably manganese dioxide. Alternatively, conductor member 16 is a multi-layered construction of film with electrically conductive and depolarizing layers blended together. Both of these alternative embodiments can be constructed according to the disclosure of PCT International Patent Publication WO 95/20350, the disclosure of which is incorporated by reference herein. The conductive interface portion of member comprises an electrically conductive layer coated on at least the side of polymeric film facing field 14 of conductive medium and the thin, depolarizing layer coated on the electrically conductive layer and contacting field 14. Because depolarizing is not needed for the mechanical and electrical contact with electrical equipment, the depolarizing layer does not need to extend to tab portion 20.

Non-limiting examples of biomedical electrodes which can use adhesive compositions of the present invention, either as conductive or nonconductive adhesive fields include electrodes disclosed in U.S. Pat. Nos. 4,524,087; 4,539,996; 4,554,924; 4,848,353 (all Engel); 4,846,185 (Carim); 4,771,783 Roberts); 4,715,382 (Strand); 5,012,810 (Strand et al.); and 5,133,356 Bryan et al.), the disclosures of which are incorporated by reference herein.

In those electrodes that also employ border areas of a nonconductive biocompatible pressure sensitive adhesive, such border areas become optional with the use of adhesive compositions of the present invention. Desirably, such border areas can be eliminated because it is no longer necessary.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, an adhesive composition of the present invention, containing an electrolyte, can reside as a field of conductive adhesive on a biomedical electrode for diagnostic (including monitoring), therapeutic, or electrosurgical purposes.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The adhesive of the present invention can be used as the ionically conductive medium in any of the embodiments shown therein. Preferably, the adhesive of the present invention is used as the field of conductive adhesive in the biomedical electrode of the embodiment shown in FIGS. 2, 3, and 4 of U.S. Pat. No. 5,012,810.

Figure 3:
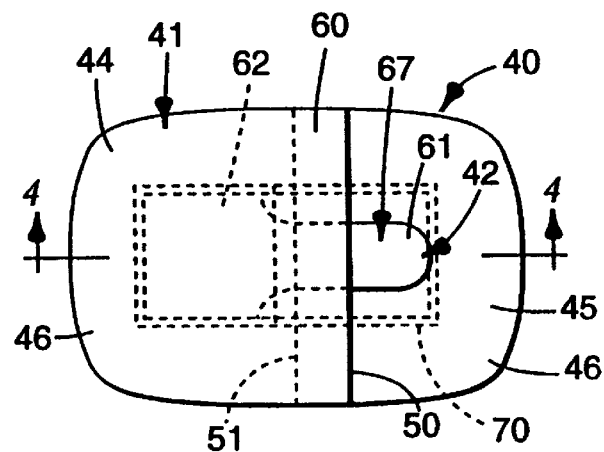
FIG. 3 is a top plan view of a monitoring biomedical electrode containing an adhesive composition of the present invention, used for longer term diagnosis or monitoring of heart conditions.
Figure 4:
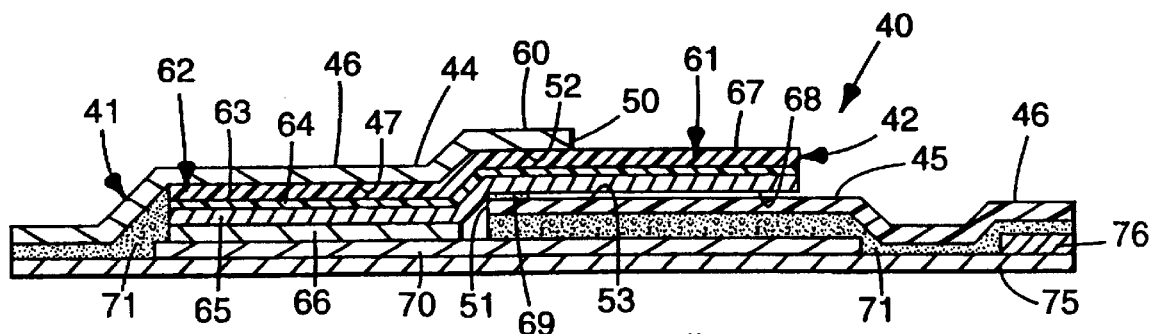
FIG. 4 is a cross-sectional view of the monitoring biomedical electrode of FIG. 3.

FIGS. 3 and 4 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 3, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment, conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of PCT Patent Publication WO 94/26950.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2 in order to enhance mechanical contact.

In general, electrode 40 is constructed such that tab portion 61 of conductor member 42 projects through seam 60 and over a portion of surface or side 46. As a result, as seen in FIGS. 3 and 4 pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 4, lower surface 68 of tab portion 61 is shown adhered in position to section 45, by means of double-stick tape strip 69. That is, adhesion in FIG. 4 between the tab portion 61 and section 45 is by means of adhesive 69 underneath tab portion 61.

In FIG. 4, a field 70 of conductive adhesive of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon. However, because of the polar, lipophilic pressure sensitive adhesive properties of the adhesive present invention, field 71 can be eliminated or can be also the adhesive of the present invention.

In FIG. 4, a layer of release liner 75 is shown positioned against that side of electrode 40 which has optional skin adhesive 71, conductive adhesive 70 and pad portion 62 thereon. Optionally as shown in FIG. 4, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, nonwoven pads, especially polyester non-wovens, various types of paper, and transparent films. Nonlimiting examples of transparent films include polyester film such as a "Melinex" polyester film commercially available from ICI Americas, Hopewell, Va. having a thickness of 0.05 mm and a surgical tape commercially available from 3M Company as "Transpore" unembossed tape.

The most preferred materials are non-woven pads made from melt blown polyurethane fiber, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No. 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications.

It will also be understood that a variety of materials may be utilized as the skin adhesive, if lipophilic, polar pressure sensitive adhesive is not employed or if the field 71 is not eliminated. Typically, acrylate ester adhesives will be preferred. Acrylate ester copolymer adhesives are particularly preferred. Such material are generally described in U.S. Pat. Nos. 2,973,826; Re 24,906; Re 33,353; U.S. Pat. Nos. 3,389,827; 4,112,213; 4,310,509; 4,323,557; 4,732,808; 4,917,928; 4,917,929; and European Patent Publication 0 051 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

It will be understood that the dimensions of the various layers, and their conformation during association, are shown somewhat exaggerated in FIG. 4, to facilitate an understanding of the construction. In general, an overall substantially flat appearance with only a very minor "s" type bend in the conductive member 42 is accommodated by the arrangement, despite the multi-layered construction of member 42.

Figure 5:
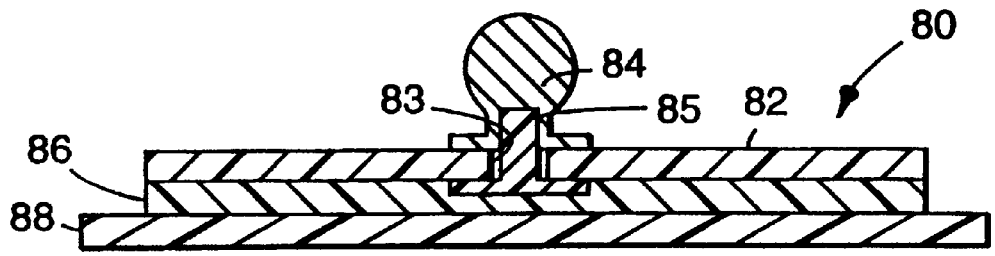
FIG. 5 is a cross-sectional view of another monitoring biomedical electrode containing an adhesive compositon of the present invention and a stud connector.

Another biomedical electrode construction is shown in FIG. 5 in cross-section. Electrode 80 has a nonconductive backing 82 having an opening 83 covered by snap 84 though which stud or eyelet 85 protrudes. The snap 84 is secured to eyelet 85 to provide a point of electrical connection to electrical instrumentation. Covering eyelet 85 and backing 82 is a field 86 of the adhesive of the present invention. A release liner 88 protects the PSA field 86 prior to use. Backing 82 can be made of the same or similar materials as insulator construction 41. Eyelet 85 can be a plastic, metallic plated eyelet (such as an ABS plastic eyelet silver-plated and chlorided and commercially available from Micron Products of Fitchburg, Mass.). Snap 84 can be a metallic snap (such as stainless steel eyelet No. 304 commercially available from Eyelets for Industry of Thomason, CN). Electrode 80 is particularly preferred because the adhesive of the present invention can serve both as the biocompatible skin adhesive and as the ionically conductive medium in the electrode 80. By comparison, a monitoring electrode that requires a skirt of biocompatible skin adhesive to surround a nonadhesive but ionically conductive gel pad, such as a Red Dot™ brand electrode commercially available from Minnesota Mining and Manufacturing Company is a more complicated construction.

Other examples of biomedical electrodes which can use the present invention as a conductive adhesive include electrodes disclosed in U.S. Pat. Nos. 4,527,087; 4,539,996; 4,554,924; 4,848,353 (all Engel); 4,846,185 (Carim); 4,771,783 Roberts); 4,715,382 (Strand); 5,133,356 (Bryan et al.), the disclosures of which are incorporated by reference herein. Methods of making such electrodes are disclosed in such patents, except that adhesive of the present invention can be substituted for the field of conductive adhesive and optionally also the field of skin adhesive disclosed in such patents. Among these various electrode constructions is an electrode construction particularly preferred as that shown in FIGS. 4 and 5 of U.S. Pat. No. 4,848,353 (Engel) in which the electrically conductive adhesive 36 is replaced by the adhesive of the present invention, and in which the biocompatible PSA 32 is optionally eliminated or optionally replaced by the adhesive of the present invention.

When used for diagnostic EKG procedures, electrodes shown in FIGS. 1 and 2 or those electrodes shown in U.S. Pat. No. 4,539,996 are preferred. When used for monitoring electrocardiogram (ECG) procedures, electrodes shown in FIGS. 3 and 4 and those disclosed in U.S. Pat. Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto.

Medical Skin Coverings

Medical skin coverings employing adhesive compositions of the present invention, optionally having antimicrobial and other biologically active agents contained therein, are useful for treatment of mammalian skin or mammalian skin openings, preferably against the possibility of infection and also for the transmission of moisture vapor and exudate from skin.

Figure 6:
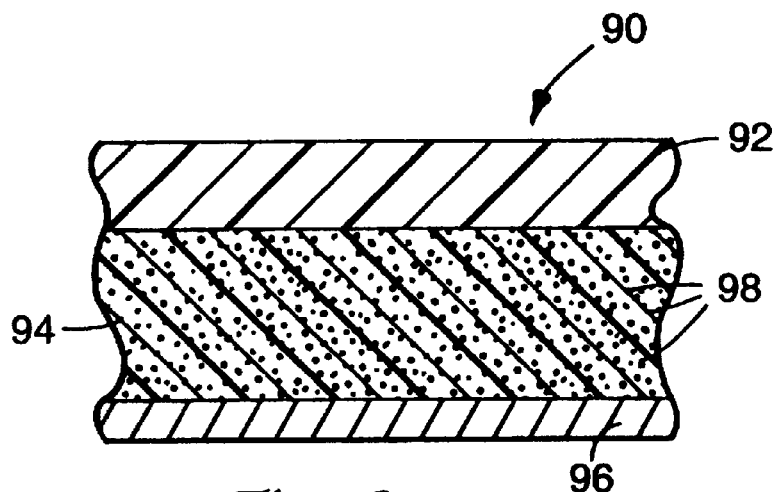
FIG. 6 is a sectional view of a medical mammalian skin covering containing adhesive composition of the present invention.

FIG. 6 shows a sectional view of a medical skin covering 90 having a backing material 92, a layer 94 of adhesive of the present invention coated on backing material 92, and protected until use by a release liner 96. Preferably, antimicrobial 98 is contained in layer 94 by adding agent 98 prior to coating on backing material 92. Alternatively, layer 94 can be used as a caulkable sealant according to U.S. Pat. No. 4,931,282 (Asmus et al.), the disclosure of which is incorporated by reference herein.

For use, the release liner 96 is removed and the layer 94 of adhesive of the present invention can be applied to the skin of the patient as a part of a medical tape, a wound dressing, a bandage of general medicinal utility, or other medical device having water or moisture absorbing properties.

The adhesive layer 94 may be coated on a layer of backing material 92 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel® 4056" and "Hytrel® 3548" branded polyester elastomers available from E. I. DuPont de Nemours and Company of Wilmington, Del., "Estane" branded polyurethanes available from B. F. Goodrich of Cleveland, Ohio or "Q-thane" branded polyurethanes available from K. J. Quinn & Co. of Malden, Mass.

The layer 94 of adhesive of the invention combined with a layer 92 of suitable backing material can be used as a dressing.

Adhesive compositions of the present invention can be used as discrete gel particles dispersed in a continuous pressure-sensitive adhesive matrix to form a two phase composite useful in medical applications, as described in U.S. Pat. No. 5,270,358, the disclosure of which is incorporated by reference herein.

The adhesive layer 94 can be coated on the backing layer 92 by a variety of processes, including, direct coating, lamination, and hot lamination. The release liner 96 can thereafter be applied using direct coating, lamination, and hot lamination.

The methods of lamination and hot lamination involve the application of pressure, or heat and pressure, respectively, on the layer of adhesive layer 94 to the backing material layer 92. The temperature for hot lamination ranges from about 50° C. to about 250° C., and the pressures applied to both lamination and hot lamination range from 0.1 Kg/cm$^2$ to about 50 Kg/cm$^2$.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 7:
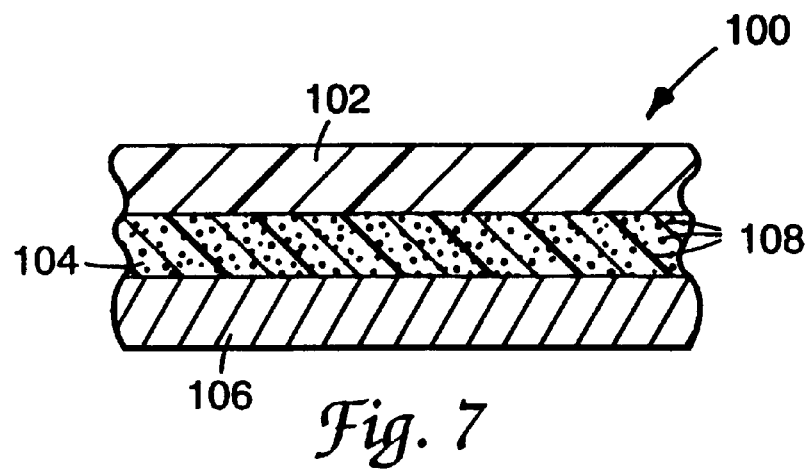
FIG. 7 is a sectional view of a pharmaceutical delivery device containing an adhesive composition of the present invention.

FIG. 7 shows a sectional view of a transdermal or topical drug delivery device 100 having a backing layer 102, a layer 104 containing adhesive of the present invention coated thereon and protected by a release liner 106. Other layers can be present between layer 102 and layer 104 to house pharmaceuticals or other therapeutic agents. Otherwise, as shown in FIG. 7, pharmaceutical and other agents 108 are dispersed in adhesive layer 104.

The backing layer 102 can be any backing material known to those skilled in the art and useful for drug delivery devices. Non-limiting examples of such backing materials are polyethylene, ethylene-vinyl acetate copolymer, polyethylene-aluminum-polyethylene composites, and ScotchPak™ brand backings commercially available from Minnesota Mining and Manufacturing Company of St. Paul, Minn.

The release liner 106 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand ScotchPak™ release liners.

The therapeutic agent 108 can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224 and 4,855,294; and PCT Patent Publication WO 89/07951.

The method of manufacturing a transdermal delivery device depends on its construction.

The drug delivery device 100 shown in FIG. 7 can be prepared using the following general method. A solution is prepared by dissolving the therapeutic agent 108 and such optional excipients as are desired in a suitable solvent and mixed into the precursor prior to forming the composition, during the formation of the composition, or directly into the already formed composition. The resulting loaded adhesive composition is coated on the backing layer 102. A release liner 106 is applied to cover loaded adhesive layer 104.

EXAMPLES

Preparation Example

For examples 1–26 and comparative examples 1–3, and 6, the plasticizing solution is prepared by dissolving a water-soluble salt in water and adding a polar organic compound. The crosslinker and the photoinitiator are dissolved in the hydrophilic polymerizable monomer. Both solutions are mixed and stirred until they are homogeneous. The surfactant and the water-adsorbing component are then added and the whole mixture is stirred again.

The mixture is coated at a caliper of 0.8 mm on to a 75 μm polyester film and covered with a siliconized 75 μm polyester film. This construction is then irradiated 6 min with a UV lamp (wavelength 351 nm, intensity 1 mW/cm$^2$, dose 360 mJ/cm$^2$).

The siliconized polyester film is removed and the adhesive with the remaining polyester film is used to determine its properties.

The following adhesion and impedance tests were carried out:
1. Adhesion
    a) A 10 mm wide strip of adhesive on polyester film was laid with its adhesive side onto a 100 μm coextruded polyethylene film and overrolled twice with a 2 kg roller. The surface consists of high density polyethylene (HDPE) and has a matte finish. The strip was peeled from the surface with a speed of 300 mm/min. with an angle of 180° and adhesion was measured with a tensile tester (in N/dm). Tests were carried out after 1 min and 24 hours storage (dwell time) at room temperature. In some examples the adhesion after 24 hours at 98% relative humidity and 37° C. was measured.
    b) The same tests were carried out with the same polyethylene film that was contaminated with a 5% solution of olive oil/oleic oil/linoleic oil/squalene (70/15/10/5) in isopropanol by soaking a tissue into the solution and wiping over the HDPE surface. The test strip was applied after the isopropanol had evaporated and the surface was wiped once more with a clean tissue. The amount of contaminant was determined to be 0.03 mg/cm$^2$. Olive oil is a triglyceride made up of fatty acids including linear saturated C16 (palmitic acid, 14%), mono-unsaturated C18 (oleic acid, 71%), and di-unsaturated C18 (linoleic acid, 10%) as described in The Encyclopedia of Chemical Technology, Fourth Edition, Volume 10, p. 267, John Wiley and Sons, New York, 1993. Thus this mixture of 70% triglyceride, 25% free fatty acid, and 5% squalene approximates both chemically and in concentration the skin surface lipids described earlier.
2. Impedance
    Gel-to-gel impedance (Back-to-back) impedance was measured according to "American National Standard for Pregelled ECG Disposable Electrodes" (ANSI/AAMI EC12-1983) with Prep-Check Model EIM105 from General Devices of Bogota, N.J. Adhesive samples were laminated to a silver backing and die cut into electrode shape. The polyester was removed and two electrodes were connected with their adhesive sides and combined with the wires of the Prep-Check Instrument. Impedance Value was read 1 minute after connection to the instrument (in Kohms).
3. Evaluation of Skin Irritation Potential The Primary Skin Irritation (PSI) test on New Zealand white rabbits is widely recognized as a predictor of the potential for skin irritation in humans as described in Chapter 10, "Predictive Skin Irritation Tests in Animals and Humans", Esther Patrick and Howard Maibach, in *Dermatotoxicology*, Fourth Edition, Francis Marzulli and Howard Maibach, Editors, Hemisphere Publishing Corp., New York, 1991. Such a test meets the irritation testing requirements of the "Tripartite Biocompatibility Guidance for Medical Devices" prepared by Toxicology Sub-group of the Tripartite Sub-Committee on Medical Devices, September 1986 which directs the testing required to substantiate the safety of materials in a medical device. The test involves clipping the hair from the back and flanks of each of six animals, selecting two test sites lateral to the midline of the back approximately ten centimeters apart. One of the two sites is abraded by making four epidermal incisions in a crosshatch pattern. One square inch of the adhesive to be tested is applied to the abraded and intact sites on each animal and secured. The trunk of each animal is wrapped with impervious plastic sheeting to occlude the test article during the one day exposure period. One hour and two days after removal of the test article, the intact and abraded test sites are examined and scored separately for erythema and edema on a graded scale of 0 to 4 as outlined in Table 1 of Patrick and Maibach cited above. The mean scores (averaged over the six animals) for erythema and edema at both the abraded and intact sites at both one hour and two days after removal are totaled and divided by four to obtain the mean primary irritation index. This is assigned a descriptive primary skin irritation rating as follows:

| Mean Primary Irritation Score | Descriptive Rating |
| --- | --- |
| 0 | Non-irritating |
| 0.1–0.5 | Minimally Irritating |
| 0.6–1.5 | Slightly Irritating |
| 1.6–3.0 | Mildly Irritating |
| 3.1–5.0 | Moderately Irritating |
| 5.1–6.5 | Severely Irritating |
| 6.6–8.0 | Extremely Irritating |

Past experience has shown that adhesives with scores of 3.0 or less (i.e. at most mildly irritating) on this scale of 8 are acceptable for use in biomedical electrode testing, presenting low risk of skin irritation during human trials.

Examples 1 to 4 and Comparative Examples 1–3

In Examples 1 to 4 and comparative examples 1–3, the peel adhesion of adhesives containing increasing amounts of surfactant was measured. The compositions of the adhesives are shown in Table 1 and were obtained by systemically increasing the level of surfactant while holding other components constant. The results of 180° peel adhesion test at room temperature to HDPE film and oil contaminated HDPE film (N/dm) are shown in Table 2.

TABLE 1

| Example | Comp. Example 1 | Comp. Example 2 | 1 | 2 | 3 | 4 | Comp. Example 3 |
|---|---|---|---|---|---|---|---|
| Components | | | percent by weight | | | | |
| Water | 15.75 | 14.34 | 13.16 | 12.16 | 11.30 | 10.56 | 15.75 |
| KCl | 1.18 | 1.08 | 0.99 | 0.97 | 0.85 | 0.79 | 1.18 |
| PEG 300 | 39.38 | 35.85 | 32.90 | 30.40 | 28.26 | 26.39 | 39.38 |
| Acrylic acid | 35.44 | 37.27 | 29.69 | 37.36 | 25.43 | 23.75 | 35.44 |
| Irgacure ® [1] 651 | 0.075 | 0.068 | 0.063 | 0.058 | 0.054 | 0.050 | 0.075 |
| TEGDA | 0.295 | 0.267 | 0.247 | 0.228 | 0.292 | 0.198 | 0.295 |
| Technocel ® [2] 30/2 | 7.88 | 7.17 | 6.58 | 6.08 | 5.65 | 5.28 | 7.88 |
| Lamesorb ® [3] SMS-20 | 0 | 8.96 | 16.45 | 27.80 | 28.26 | 32.99 | 0 |

[1] 2,2-Dimethoxy-2-phenylacetophenone; photoinitiator commercially available from Ciba Geigy, Hawthorne, New York
[2] Cellulose powder commercially available from CFF (Cellulose Füllstoff Fabrik), Mönchengladbach, Germany
[3] Sorbitol fatty ester ethoxylates commercially available from Chemische Fabrik Grünau, Illertissen, Germany

TABLE 2

| Example Dwell time | Comp. Example 1 | Comp. Example 2 | 1 | 2 | 3 | 4 | Comp. Example 3 |
|---|---|---|---|---|---|---|---|
| 1 min | 3.6 | 6.9 | 11.9 | 11.5 | 12.0 | 11.1 | 5.4 |
| 1 min. (oil) | <0.1 | <0.1 | 2.3 | 4.3 | 3.9 | 5.8 | <0.1 |
| 24 h | 4.4 | 8.0 | 12.4 | 13.3 | 12.4 | 12.6 | 6.2 |
| 24 h (oil) | <0.1 | 0.5 | 5.9 | 10.0 | 9.3 | 8.8 | <0.1 |

From the above Table 2 it can be seen that the inventive conductive adhesives containing increasing amounts of surfactant show good adhesion as well as to a HDPE film as to a HDPE film contaminated with oil after both one minute and after 24 hour dwell. The peel adhesion value from the oil-contaminated HDPE surface is at least 15% of the peel adhesion value obtained from the same HDPE surface that has not been contaminated with oil providing that the level of surfactant is high enough.

Examples 5 to 9 and Comparative Examples 4–6

In examples 5 to 9 and comparative examples 4–6, the peel adhesion of adhesives containing surfactants of different HLB-values are measured. The results of 180° peel adhesion test at room temperature to HDPE film and oil contaminated HDPE film (N/dm) are shown in Table 3.

Each composition of examples 5–9 and comparative example 6 contains

| | Percent by wt. |
|---|---|
| Water | 16 |
| KCl | 2 |
| PEG 300 | 70 |
| Acrylic Acid | 36 |
| Irgacure ® [1] 651 | 0.076 |
| TEGDA | 0.3 |
| Technocel ® [2] 30/2 | 8.0 |
| Surfactant | 50 |

The peel adhesion on a HDPE film and on a HDPE film contaminated with oil of the conductive adhesives of the invention and of commercial available conductive adhesives was measured at room temperature. The results are shown in Table 3.

TABLE 3

| Example | 5 | 6 | 7 | 8 | 9 |
|---|---|---|---|---|---|
| Surfactant | Lamesorb ® [1] SMS-20 | Tergitol ® [2] TMN 6 | Igepal ® [3] 520 | Arosurf ® [4] 66 E 20 | Lamesorb ® [1] SMS-20/ Tergitol ® [2] TMN6 (2:1) |
| HLB-value | 14.9 | 11.7 | 10.0 | 15.0 | — |
| Dwell time | | | | | |
| 1 min. | 7.4 | 9.7 | 3.8 | 6.7 | 5.0 |
| 1 min. (oil) | 5.3 | 2.0 | 1.2 | 0.9 | 4.7 |
| 24 h | 7.4 | 10.2 | 6.3 | 5.8 | 6.4 |
| 24 h (oil) | 8.6 | 8.3 | 5.1 | 5.1 | 5.6 |

| Comparative Example | 4 | 5 | 6 |
|---|---|---|---|
| Electrode | 3M Red Dot 2330 | Promeon ™ | Tergitol ® [2] TMN 3 |
| HLB-value | — | — | 8.3 |

TABLE 3-continued

| Dwell time | | | |
|---|---|---|---|
| 1 min. | 10.0 | 7.4 | 11.0 |
| 1 min. (oil) | <0.16 | 0.12 | 0.4 |
| 24 h | 13.1 | 8.7 | 9.4 |
| 24 h (oil) | 1.7 | 1.4 | 0.8 |

[1]Sorbitol fatty ester ethoxylates commercially available from Chemische Fabrik Grünau, Illertissen, Germany
[2]Isoalkoxylates commercially available from Union Carbide Chemicals, Danbury, Connecticut
[3]Octylphenolethoxylate commercially available from Rhône Poulenc, Cranbury, New Jersey
[4]PEG-20-Isostearylether commercially available from Sherex Chemical Co., Dublin, Ohio
Promeon ™ is commercially available from Ludlow Corporation, Chicopee, Massachusetts.

From the above Table 3 it can be seen that the inventive conductive adhesives show good adhesion as well as to a HDPE film as to a HDPE film contaminated with oil. The adhesion to the HDPE film contaminated with oil of commercial available electrodes containing adhesives of the state of art decreases to a value of less 15% of the peel adhesion of the value obtained from the same HDPE surface that has not been contaminated with oil as shown in comparative examples 4 and 5. Comparative example 6 demonstrates that use of a surfactant with an HLB value of 8.3 also does not give adhesion to the oil contaminated film. The adhesion is not sufficient for the use as an electrode over a long application period.

Examples 10–14

In Examples 10–14, the peel adhesion of adhesives containing increasing amounts of cellulose derivative was measured. The compositions of the adhesives are shown in Table 4, the results of 180° peel adhesion test at room temperature to HDPE film and oil contaminated HDPE film (N/dm) are shown in Table 5.

TABLE 4

| Example | 10 | 11 | 12 | 13 | 14 |
|---|---|---|---|---|---|
| Components | percent by weight | | | | |
| Water | 18.0 | 18.0 | 18.0 | 18.0 | 18.0 |
| KCl | 2.0 | 2.0 | 2.0 | 2.0 | 2.0 |
| PEG 300 | 40.0 | 40.0 | 40.0 | 40.0 | 40.0 |
| Acrylic acid | 36.0 | 36.0 | 36.0 | 36.0 | 36.0 |
| Irgacure ® [1] 651 | 0.076 | 0.076 | 0.076 | 0.076 | 0.076 |
| TEGDA | 0.3 | 0.3 | 0.3 | 0.3 | 0.3 |
| Technocel ® [2] 30/2 | 2.0 | 4.0 | 6.0 | 10.0 | 12.0 |
| Lamesorb ® [3] SMS-20 | 50.0 | 50.0 | 50.0 | 50.0 | 50.0 |

[1]2,2-Dimethoxy-2-phenylacetophenone, photoinitiator commercially available from Ciba Geigy, Hawthorne, New York
[2]Cellulose powder commercially available from CFF (Cellulose Füllstoff Fabrik), Mönchengladbach, Germany
[3]Sorbitol fatty ester ethoxylates commercially available from Chemische Fabrik Grünau, Illertissen, Germany

TABLE 5

| Example Dwell time | 11 | 12 | 13 | 14 | 15 |
|---|---|---|---|---|---|
| 1 min. | 12.6 | 14.2 | 14.2 | 13.8 | 14.6 |
| 1 min. (oil) | 6.7 | 6.3 | 5.5 | 6.3 | 5.9 |
| 24 h | 14.6 | 14.6 | 15.0 | 16.5 | 15.0 |
| 24 h (oil) | 13.8 | 11.0 | 12.2 | 15.0 | 14.2 |

TABLE 5-continued

| Example Dwell time | 11 | 12 | 13 | 14 | 15 |
|---|---|---|---|---|---|
| 24 h humidity | 7.1 | 6.7 | 6.3 | 12.6 | 15.0 |
| 24 h humidity (oil) | 4.3 | 5.9 | 12.6 | 17.7 | 13.0 |

From Table 5 it can be seen that the inventive conductive adhesives containing increasing amounts of a cellulose derivative show good adhesion as well as to a HDPE film as to a HDPE film contaminated with oil. The peel adhesion value from the oil-contaminated HDPE surface is at least 15% of the peel adhesion value obtained from the same HDPE surface that has not been contaminated with oil. An improvement in adhesion to both surfaces under humid conditions is noted as the level of cellulose derivative is increased.

Examples 15–20

In Examples 15 to 20, the peel adhesion of adhesives containing increasing amounts of KCl was measured. The compositions of the adhesives are shown in Table 6. The results of 180° peel adhesion test at room temperature to HDPE film and oil contaminated HDPE film (N/dm) are shown in Table 7.

TABLE 6

| Example | 15 | 16 | 17 | 18 | 19 | 20 |
|---|---|---|---|---|---|---|
| Components | percent by weight | | | | | |
| Water | 16.0 | 16.0 | 16.0 | 16.0 | 16.0 | 16.0 |
| KCl | — | 0.4 | 0.8 | 1.2 | 1.6 | 2.0 |
| PEG 300 | 40.0 | 40.0 | 40.0 | 40.0 | 40.0 | 40.0 |
| Acrylic acid | 36.0 | 36.0 | 36.0 | 36.0 | 36.0 | 36.0 |
| Irgacure ® [1] 651 | 0.076 | 0.076 | 0.076 | 0.076 | 0.076 | 0.076 |
| TEGDA | 0.3 | 0.3 | 0.3 | 0.3 | 0.3 | 0.3 |
| Technocel ® [2] 30/2 | 8.0 | 8.0 | 8.0 | 8.0 | 8.0 | 8.0 |
| Lamesorb ® [3] SMS-20 | 50.0 | 50.0 | 50.0 | 50.0 | 50.0 | 50.0 |

[1]2,2-Dimethoxy-2-phenylacetophenone, photoinitiator commercially available from Ciba Geigy, Hawthorne, New York
[2]Cellulose powder commercially available from CFF (Cellulose Füllstoff Fabrik), Mönchengladbach, Germany
[3]Sorbitol fatty ester ethoxylates commercially available from Chemische Fabrik Grünau, Illertissen, Germany

TABLE 7

| Example dwell time | 16 | 17 | 18 | 19 | 20 | 21 |
|---|---|---|---|---|---|---|
| 1 min. | 11.0 | 12.2 | 13.4 | 12.6 | 13.4 | 15.4 |
| 1 min. (oil) | 9.1 | 11.0 | 10.2 | 11.0 | 11.8 | 12.2 |
| 24 h | 12.6 | 12.6 | 14.6 | 14.6 | 14.6 | 15.4 |
| 24 h (oil) 13.8 | 13.8 | 10.2 | 16.5 | 12.2 | 14.2 | 18.9 |
| 24 h humidity | 17.1 | 10.2 | 16.1 | 12.2 | 14.2 | 14.6 |
| 24 h humidity (oil) | 11.0 | 13.0 | 11.0 | 7.1 | 13.4 | 16.6 |

From the above Table 7 it can be seen that the inventive conductive adhesives that contain increasing amounts of a water soluble salt (KCl) show good adhesion as well as to a HDPE film as to a HDPE film contaminated with oil. The peel adhesion value from the oil-contaminated HDPE surface is at least 15% of the peel adhesion value obtained from the same HDPE surface that has not been contaminated with oil.

Examples 22 to 26

In examples 22 to 26 the skin irritation potential of adhesives containing different surfactants was assessed using the test methodology described above. Results, shown in Table 8, demonstrate that adhesive formulations can have slight or mild irritation potential.

TABLE 8

| Example | 22 | 23 | 24 | 25 | 26 |
|---|---|---|---|---|---|
| Components | \multicolumn{5}{c}{Percent by Weight} | | | | |
| Water | 28.0 | 28.0 | 28.0 | 18.0 | 18.0 |
| KCl | 2.0 | 2.0 | 2.0 | 2.0 | 2.0 |
| Methoxy PEG 350 | 15.0 | 15.0 | 15.0 | 15.0 | 15.0 |
| Acrylic acid | 24.83 | 24.83 | 24.83 | 29.67 | 29.69 |
| Irgacure 651 | 0.07 | 0.07 | 0.07 | 0.07 | 0.07 |
| Methylene bis(acrylamide) | 0.10 | 0.10 | 0.10 | | |
| Triethylene glycol bis(methacrylate) | | | | 0.26 | 0.24 |
| Arosurf ® [1] 66PE12 | 30.0 | | | | |
| Arosurf ® [2] 66E20 | | 30.0 | | | |
| Brij ® [3] 97 | | | 30.0 | | |
| Surfonic ® [4] L24-7 | | | | 35.0 | |
| Tergitol ® [5] 15-S-9 | | | | | 35.0 |
| PSI | 2.2/8.0 | 1.1/8.0 | 2.4/8.0 | 1.6/8.0 | 1.0/8.0 |

[1]PPG-3-PEG-9 Isostearyl ether (HLB 12.2) available from Sherex Chemical Company, Dublin, Ohio
[2]PEG-20 Isostearyl ether (HLB 15.0) available from Sherex Chemical Company, Dublin, Ohio
[3]PEG-10 Oleyl ether (HLB 12.4) available from ICI, Wilmington, Delaware
[4]PEG-7 C12–14 alkyl ether available from Texaco Chemical Company, Houston, Texas
[5]PEG-7 sec-C11-15 alkyl ether (HLB 12.4) available from Union Carbide, Danbury,CT Examples 27 and 28

To a solution of 20 g potassium chloride in 1580 g deionized water and 200 g PEG 300 was added 200 g micronized poly(N-vinyl pyrrolidone) (available from ISP, Wayne, N.J.) which had been lightly crosslinked by exposure to gamma irradiation. The use of such formulations for ionically conductive adhesives is described in U.S. Pat. No. 5,276,079. After stirring for two hours with a air-driven overhead stirrer, a 500 g portion of this viscous 21% solids precursor was formulated further with either 71.4 g 70% solids Glucopon® 225CS (a C8–10 alkylated polyglycoside (HLB 13.6) available from Henkel—Example 27) or 50 g Varamid LL1 (the diethanolamide of lauric acid available from Sherex Chemical Company, Dublin, Ohio—Example 28). The resulting solutions were coated at 1.01 mm thick onto 0.07 mm clear polyester film, dried in a 93° C. forced air oven for 30 minutes yielding formulations that are 32.3 weight percent poly(N-vinyl pyrrolidone), 32.3 weight percent PEG 300, 32.3 weight percent surfactant, and 3.2 weight percent KCl. After conditioning overnight in a humidity chamber at 60% RH and 24° C. to partially rehydrate, adhesion testing was conducted as described above and results (shown in Table 9) demonstrate applicability of this technology to other polar adhesives.

TABLE 9

| Example | 27 | 28 |
|---|---|---|
| Dwell time | | |
| 1 min | 27.7 | 16.8 |
| 1 min (oil) | 3.7 | 5.1 |
| 24 hour | 54.9 | 34.8 |
| 24 hour (oil) | 29.8 | 30.6 |

For an appreciation of the scope of the invention, the claims follow.

What is claimed is:

1. A skin compatible, lipophilic, polar pressure-sensitive adhesive, comprising a hydrophilic polymer matrix and a plasticizer in an amount sufficient to render the matrix cohesive and pressure-sensitive adhesive, wherein the plasticizer comprises a water-soluble polar organic compound and a compatible surfactant or mixture of compatible surfactants present in an amount of at least 9 weight percent of the adhesive, wherein the compatible surfactant has a HLB-value of 10 to 17 or wherein the mixture of compatible surfactants combine to have a HLB-value of 10 to 17.

2. The adhesive of claim 1, wherein the hydrophilic polymer matrix is selected from poly(ethylene oxide), natural and synthetic polysaccharides and their derivatives, and homo- and copolymers of ethylenically unsaturated hydrophilic monomers including $\alpha,\beta$-ethylenic unsaturated carboxylic acids having up to eight carbon atoms and salts thereof, acrylamide, N-vinyl pyrrolidone, hydroxyethyl (meth)acrylate, acrylamidopropane sulfonic acid and salts thereof, methyl and ethyl vinyl ethers, and polymers having ammonium functionality.

3. The adhesive according to claim 2, wherein the polymeric matrix comprises a homo- or copolymer of monomers including (meth)acrylic acid salts thereof.

4. The adhesive according to any of claims 1 to 3, wherein the water-soluble, polar organic compound is selected from mono- and polyhydric alcohols.

5. The adhesive according to claim 4, wherein the water-soluble, polar organic compound is selected from glycerol, poly(ethylene glycol), monomethoxypoly(ethylene glycol) or propanediol.

6. The adhesive according to any of claims 1 to 5, wherein the surfactant is a nonionic surfactant.

7. The adhesive according to claim 6, wherein the nonionic surfactant is selected from fatty alcohol polyglycolethers, alkyl phenylpolyglycolethers, fatty acid polyglycolesters, fatty acid amide polyglycolethers, fatty amine polyglycolethers, alkoxylated triglycerides, alk(en)yl oligoglycosides, fatty acid glucamides, polyol fatty acid esters, sugar esters, sorbitol esters and sorbitol ester ethoxylates.

8. The adhesive according to any of claims 1 to 7, further comprising a water-soluble salt in an amount up to 12% by weight of the plasticizing solution.

9. The adhesive according to claim 8, wherein the water-soluble salt is selected from sodium chloride or potassium chloride.

10. The adhesive according to any of claims 1 to 9, further comprising one or more water adsorbing components selected from cellulose, starch and pectins and their derivatives.

11. An adhesive, comprising 10 to 40 weight percent of a hydrophilic, ethylenically unsaturated monomer, 0 to 60 weight percent water, 0 to 80 weight percent of a water soluble, polar organic compound, and at least 9 weight percent compatible surfactant or mixture of compatible surfactants.

12. The adhesive of claim 11, further comprising a crosslinking agent.

13. A process for preparing the adhesive of claim 1, which comprises subjecting to free radical polymerization conditions a solution of 10 to 40 weight percent of a hydrophilic, ethylenically unsaturated monomer dissolved in 0 to 60 weight percent water, 0 to 80 weight percent of a water-soluble, polar organic compound and at least 9 weight percent, of the adhesive, of a surfactant or mixture of surfactants and a polymerization initiator for the hydrophilic monomer.

14. A process according to claim 13, wherein the free radical polymerization is carried out in the presence of ultraviolet light.

15. A biomedical electrode, comprising:
a field of adhesive conductive medium for contacting mammalian skin and a means for electrical communication for interfacing with the adhesive conductive medium and electrical diagnostic, therapeutic, or electrosurgical instrumentation, the adhesive conductive medium adhered to the means for electrical communication and comprising an adhesive according to claim 1.

16. The biomedical electrode according to claim 15, wherein the adhesive conductive medium further comprises an ionic salt electrolyte present in an amount from about 0.5 to about 5 weight percent of the adhesive conductive medium.

17. The biomedical electrode according to claim 15, wherein the adhesive conductive medium further comprises a redox couple present in an amount of not more than about 20 percent by weight of the adhesive conductive medium.

18. The biomedical electrode according to claim 15, wherein the means for electrical communication comprises a conductor member having an interface portion contacting the adhesive conductive medium and a tab portion available for mechanical and electrical contact with the electrical diagnostic, therapeutic, or electrosurgical instrumentation.

19. The biomedical electrode according to claim 15, wherein the means for electrical communication comprises a conductor member having an eyelet or snap connector contacting the adhesive conductive medium.

20. The biomedical electrode according to claim 15, wherein the means for electrical communication comprises a conductive member having a conductive layer coating at least on a side of the conductor member contacting the adhesive conductive medium.

21. The biomedical electrode according to claim 20, wherein said conductive layer coating is silver/silver chloride.

22. A mammalian skin covering comprising: an adhesive layer for contacting mammalian skin and backing layer, the adhesive layer adhered to the backing layer and comprising a polar, lipophilic pressure sensitive adhesive according to claim 1.

23. The mammalian skin covering according to claim 22, wherein the adhesive layer further comprises an antimicrobial agent.

24. The mammalian skin covering according to claim 22, wherein the backing layer comprises a film, substrate, or elastic, porous or breathable woven or nonwoven material.

25. The mammalian skin covering according to claim 22, wherein the covering comprises a medical tape, a wound dressing, a bandage of general medicinal utility, or a medical device contacting mammalian skin.

26. A pharmaceutical delivery device comprising: an adhesive layer for contacting mammalian skin and a backing layer, the adhesive layer adhered to the backing layer and comprising a polar, lipophilic pressure sensitive adhesive according to claim 1.

27. The pharmaceutical delivery device according to claim 26, wherein the adhesive layer further comprises a topical, transdermal, or iontophoretic therapeutic agent or pharmaceutical.

28. The pharmaceutical delivery device according to claim 26, wherein the adhesive layer further comprises an excipient, a solvent, or a penetration enhancing agent.

* * * * *